US008986009B2

(12) United States Patent
Völkl et al.

(10) Patent No.: US 8,986,009 B2
(45) Date of Patent: Mar. 24, 2015

(54) METHOD FOR DETERMINING 3-D DATA FROM AT LEAST ONE PREPARED MAXILLARY AREA

(75) Inventors: Lothar Völkl, Goldbach (DE); Stefan Fecher, Johannesberg (DE); Hartmut Brinkmann, Bohmte (DE); Ralf Jaumann, Bahlingen (DE)

(73) Assignee: Degudent GmbH, Hanau (DE)

( * ) Notice: Subject to any disclaimer, the term of this patent is extended or adjusted under 35 U.S.C. 154(b) by 435 days.

(21) Appl. No.: 12/991,191

(22) PCT Filed: Apr. 2, 2009

(86) PCT No.: PCT/EP2009/053955
§ 371 (c)(1),
(2), (4) Date: Jan. 11, 2011

(87) PCT Pub. No.: WO2009/135735
PCT Pub. Date: Nov. 12, 2009

(65) Prior Publication Data
US 2011/0111360 A1 May 12, 2011

(30) Foreign Application Priority Data

May 8, 2008 (DE) .......................... 10 2008 002 845

(51) Int. Cl.
*A61C 5/10* (2006.01)
*A61C 13/00* (2006.01)
*A61C 9/00* (2006.01)
(52) U.S. Cl.
CPC ............. *A61C 13/0004* (2013.01); *A61C 9/004* (2013.01)

USPC ............................................ 433/223; 700/98
(58) Field of Classification Search
USPC ............... 433/215, 219, 223, 213; 700/97–98
See application file for complete search history.

(56) References Cited

U.S. PATENT DOCUMENTS

| | | | | | |
|---|---|---|---|---|---|
| 3,979,829 | A | * | 9/1976 | Lemos | 433/165 |
| 4,144,645 | A | * | 3/1979 | Marshall | 433/223 |
| 4,353,696 | A | * | 10/1982 | Bridges | 433/125 |
| 4,411,626 | A | * | 10/1983 | Becker et al. | 433/223 |
| 4,824,367 | A | * | 4/1989 | Rosenstiel et al. | 433/75 |
| 4,837,732 | A | * | 6/1989 | Brandestini et al. | 433/29 |
| 4,997,369 | A | * | 3/1991 | Shafir | 433/72 |
| 5,003,484 | A | * | 3/1991 | Vollmayr | 700/161 |
| 5,017,139 | A | * | 5/1991 | Mushabac | 433/109 |
| 5,092,022 | A | * | 3/1992 | Duret | 29/896.1 |
| 5,128,870 | A | * | 7/1992 | Erdman et al. | 700/163 |
| 5,224,049 | A | * | 6/1993 | Mushabac | 700/163 |
| 5,257,184 | A | * | 10/1993 | Mushabac | 433/75 |
| 5,343,391 | A | * | 8/1994 | Mushabac | 433/76 |
| 5,347,454 | A | * | 9/1994 | Mushabac | 433/214 |

(Continued)

FOREIGN PATENT DOCUMENTS

EP 0580565 1/1994
EP 0943296 2/2004
WO WO 2009135735 A2 * 11/2009 ............. A61C 13/00

Primary Examiner — Cris L Rodriguez
Assistant Examiner — Hao D Mai
(74) Attorney, Agent, or Firm — Ladas & Parry LLP

(57) ABSTRACT

A process for determining 3-D data of at least one prepared jaw area, such as a prepared tooth stump, by mechanically scanning the jaw area and digitizing the measured values determined during the scanning. The jaw area is prepared with a dental instrument having positions which are optically measured during the preparation, and the 3-D data is determined from the positions of the dental instrument that are associated with the prepared jaw area.

18 Claims, 4 Drawing Sheets

(56) References Cited

U.S. PATENT DOCUMENTS

| | | | |
|---|---|---|---|
| 5,448,472 A * | 9/1995 | Mushabac | 433/70 |
| 5,545,039 A * | 8/1996 | Mushabac | 433/215 |
| 5,562,448 A * | 10/1996 | Mushabac | 433/215 |
| 5,587,912 A * | 12/1996 | Andersson et al. | 700/98 |
| 5,652,709 A * | 7/1997 | Andersson et al. | 700/161 |
| 5,688,118 A * | 11/1997 | Hayka et al. | 433/27 |
| 5,725,376 A * | 3/1998 | Poirier | 433/172 |
| 5,938,446 A * | 8/1999 | Andersson et al. | 433/223 |
| 6,000,939 A * | 12/1999 | Ray et al. | 433/27 |
| 6,030,211 A * | 2/2000 | Sandhaus | 433/76 |
| 6,212,442 B1 * | 4/2001 | Andersson et al. | 700/194 |
| 6,261,098 B1 * | 7/2001 | Persson | 433/213 |
| 6,334,773 B1 * | 1/2002 | Ahlen et al. | 433/29 |
| 6,371,930 B1 * | 4/2002 | Shafir | 600/590 |
| 6,402,707 B1 * | 6/2002 | Ernst | 600/590 |
| 6,511,323 B1 * | 1/2003 | Wilkinson | 433/223 |
| 6,691,764 B2 * | 2/2004 | Embert et al. | 164/4.1 |
| 6,786,726 B2 * | 9/2004 | Lehmann et al. | 433/223 |
| 7,153,135 B1 * | 12/2006 | Thomas | 433/213 |
| 7,172,424 B2 * | 2/2007 | Wu | 433/223 |
| 7,184,150 B2 * | 2/2007 | Quadling et al. | 356/602 |
| 7,286,954 B2 * | 10/2007 | Kopelman et al. | 702/152 |
| 7,346,417 B2 * | 3/2008 | Luth et al. | 700/117 |
| 7,457,443 B2 * | 11/2008 | Persky | 382/128 |
| 7,494,338 B2 * | 2/2009 | Durbin et al. | 433/29 |
| 7,762,814 B2 * | 7/2010 | van der Zel | 433/201.1 |
| 7,840,256 B2 * | 11/2010 | Lakin et al. | 600/426 |
| 7,965,860 B2 * | 6/2011 | Holzner et al. | 382/100 |
| 8,246,352 B2 * | 8/2012 | Takebayashi | 433/75 |
| 2001/0012606 A1 * | 8/2001 | Unger | 433/173 |
| 2003/0096214 A1 * | 5/2003 | Luthardt et al. | 433/171 |
| 2005/0095554 A1 * | 5/2005 | Wilkinson | 433/76 |
| 2008/0085828 A1 * | 4/2008 | Khan et al. | 501/152 |
| 2010/0323320 A1 * | 12/2010 | Takebayashi | 433/75 |
| 2011/0033819 A1 * | 2/2011 | Freyer et al. | 433/72 |
| 2011/0316994 A1 * | 12/2011 | Lemchen | 348/66 |
| 2012/0040305 A1 * | 2/2012 | Karazivan et al. | 433/29 |
| 2013/0209965 A1 * | 8/2013 | Fisker et al. | 433/220 |

* cited by examiner

METHOD FOR DETERMINING 3-D DATA FROM AT LEAST ONE PREPARED MAXILLARY AREA

BACKGROUND OF THE INVENTION

The invention relates to a process for determining 3-D data of at least one prepared jaw area such as a prepared tooth stump by mechanical scanning of the jaw area and digitizing the measured values determined during the scanning.

A process for the production of a denture consisting of ceramic material can be gathered from EP-A-0 580 565. In it, a prepared tooth in the mouth of a patient can be optically or mechanically photographed in order to then produce the denture from the values determined in this manner and digitized by a milling machine.

Other processes provide that an impression is taken of the prepared jaw area, in particular a tooth stump, in order to produce a positive model that is scanned and digitized (EP-B-1 067 880).

All processes, whether a direct scanning in the patient's mouth, or a scanning of an impression require a completely or almost completely prepared jaw area in order to obtain the desired 3D data. In the case of a partially defective impression or not completely scanned jaw area there is then the possibility, as a function of the software used, of supplementing missing data or of removing obviously inappropriate data in order to avoid that the denture produced is defective.

The present invention is based on the problem of further developing a process of the initially cited type in such a manner that the 3-D data required for the production of the denture can be determined without expensive scanning processes or the production of a positive model being necessary.

In order to solve the problem the invention substantially provides that the jaw area, such as a tooth stump, to be prepared is prepared with a dental instrument whose positions are optically measured during the preparation and that the 3-D data is determined from the positions of the dental instrument that are associated with the prepared jaw area. The positional data of the dental instrument during the preparation of the jaw area is used for the determination of the final contour of the prepared jaw area. Therefore, it is not necessary that the jaw area is at first prepared and is subsequently scanned with a separate apparatus. This is time-consuming and expensive on account of the various apparatuses used. In contrast thereto, according to the invention the jaw area is tactilely scanned simultaneously with the preparation of the jaw area in order to make the required digitized measured values available after the conclusion of the preparation in order to be able to make a denture.

In order to make possible the determination of the position of the dental instrument, it is provided with optically effective markings that are detected by an optical sensor for the spatial determination of the position of the dental instrument. In particular, the dental instrument is a drill for preparing the jaw area.

In general, the dental instrument should consist of a handle such as a hand grip and of a replaceable insert such as, e.g., a drill. The handle should have markings so that one and the same handle can be used for different inserts or tools.

When an insert is replaced the different effective geometry of the inserts must be taken into account and a calibration is to be carried out.

In order to ensure an unambiguous determination of the position and therewith of the geometry, it is furthermore provided that the dental instrument is calibrated before the preparation by scanning a normal such as a sphere. These types of measures are sufficiently known from the technology for measuring coordinates in conjunction with the tactile measuring of workpieces so that these previously known measures are referred to and reference is explicitly made to them.

A further development of the invention that is to be emphasized provides that the positions of the dental instrument are determined taking into consideration any movement of the jaw area. In other words, the movement data of the dental instrument is offset against the movement data of the jaw in order to be able to calculate the 3-D data record.

To this end a position sensor arranged stationarily relative to the jaw area can be associated with the jaw area. The position sensor can comprise optically effective markings stationarily associated with the jaw area and can comprise an optical sensor that detects the movement of the markings. However, an inertial platform can also be used for determining positions whose data is offset with that of the optical sensor, by means of which the movements of the dental instrument are detected.

In particular, light sources such as LEDs or optical reflectors are used for the first and/or second optically effective markings. In the latter instance it is necessary that the reflectors are loaded with light in order to be able to detect the reflected light with the optical sensor such as a camera.

The 3-D data corresponding to the prepared jaw area is then processed in order to produce a denture by a software, in particular CAD software, which denture can fit on the jaw area, in order to then produce the desired denture by a CAM program from a blank, in particular consisting of porous and pre-sintered ceramic material. This basically takes place by milling. However, the denture can alternatively also be produced on the basis of the 3-D data in a building-up process such as rapid prototyping.

A further embodiment of the invention to be emphasized provides that the inner contour of the denture is determined and calculated from the 3-D data determined by the positional determinations of the dental instrument and that the outer contour is determined and calculated from determined digitized data and/or data taken from a library from scanning the jaw area surrounding the jaw area to be provided with the denture.

The teaching of the invention, the working of the jaw area and the simultaneous determination of the final contour in a single process have the advantage that measuring uncertainties during touching present regarding tactile measuring do not occur. As regards intraoral scanners, there is the advantage that no preparation edge must be exposed because it is frequently required during contactless scanning that the gum on the preparation boundary is pressed away by a thread. Translucency of the tooth or liquid in the jaw area are not a problem during the determination of the contour. Problematic gingiva is pressed away by the dental instrument during the preparation.

In particular, a rotating tool such as a drill is used as dental instrument in which the receptacle or handle of the rotating tool has at least three optical markings such as light-emitting diodes that are detected by a receiver in order to detect the spatial position of the tool in this manner. Due to the ability of the rotating tool to be replaced, it is necessary when using a new rotating tool that a calibration or teaching takes place on a normal such as a reference sphere.

According to the invention an outline is formed during the preparation that corresponds to the form of the prepared jaw area such as a tooth stump. The movement of the patient is additionally considered in order to avoid measuring errors.

In particular, the process of the invention is used to produce caps, a frame or an inlay. An exceedingly precise determination of contour takes place.

In contrast to the above, it is basically not necessary to take into account a possible relative movement of the jaw area to be prepared to the jaw itself since the cutting forces occurring during the preparation are so small that distortions of the measured values are excluded.

In order to initiate a measuring procedure the cutting in of the tool or, e.g., a power change of the tool can be used that occurs when the drill comes in contact with the jaw area to be prepared and the working begins.

In the case of a drill as dental instrument the movement of a rotating tool guided by the preparing person such as a dentist is detected. In order to detect the movements of the drill several optical markings such as LEDs are applied on it or on its holder. The calibration of the tip of the rotating tool to the optical marking takes place by touching a normal such as a reference sphere at several positions.

In order to detect the movement of the jaw a platform with at least three optical markings or an inertial platform is stationarily connected to the jaw. The sensor detecting the jaw movement can be fastened on a face leading to the jaw or in a bite block arranged between the lower and the upper jaw. The jaw movement can be detected by the optical sensor that determines the movement of the dental instrument. However, a separate sensor can also be used that stands in a stationary relationship to the optical sensor for the dental instrument.

In order to also digitize areas that are not prepared, it is provided that the dental instrument scans the areas of the jaw area such as at least one tooth and if required necessary parts of the jaw ridge, which areas are not provided for working in the course of the treatment phase. This yields data that can be used for the calculation of the outer contour of a denture to be produced.

Independently of the above, a further development provides that the preparation boundary is determined with a separate feeler or with an insert such as a feeler pin which insert can be provided with a dental instrument or its handle.

According to the invention a dental instrument used to prepare a jaw area is used at the same time as an oral scanner.

Further details, advantages and features of the invention result not only from the claims, the features to be gathered from them whether alone and/or in combination but also from the following description of preferred exemplary embodiments to be gathered from the drawings.

DETAILED DESCRIPTION OF THE INVENTION

Figure 1:
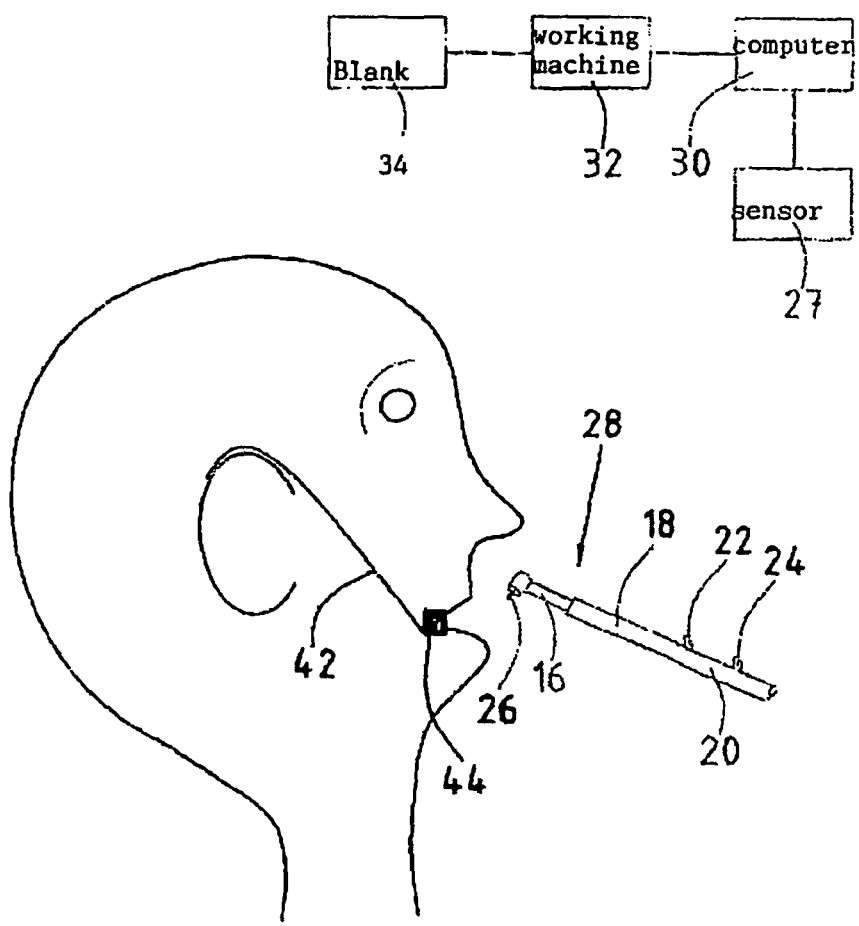
FIG. 1 shows a basic view for explaining the process in accordance with the invention.
Figure 2:
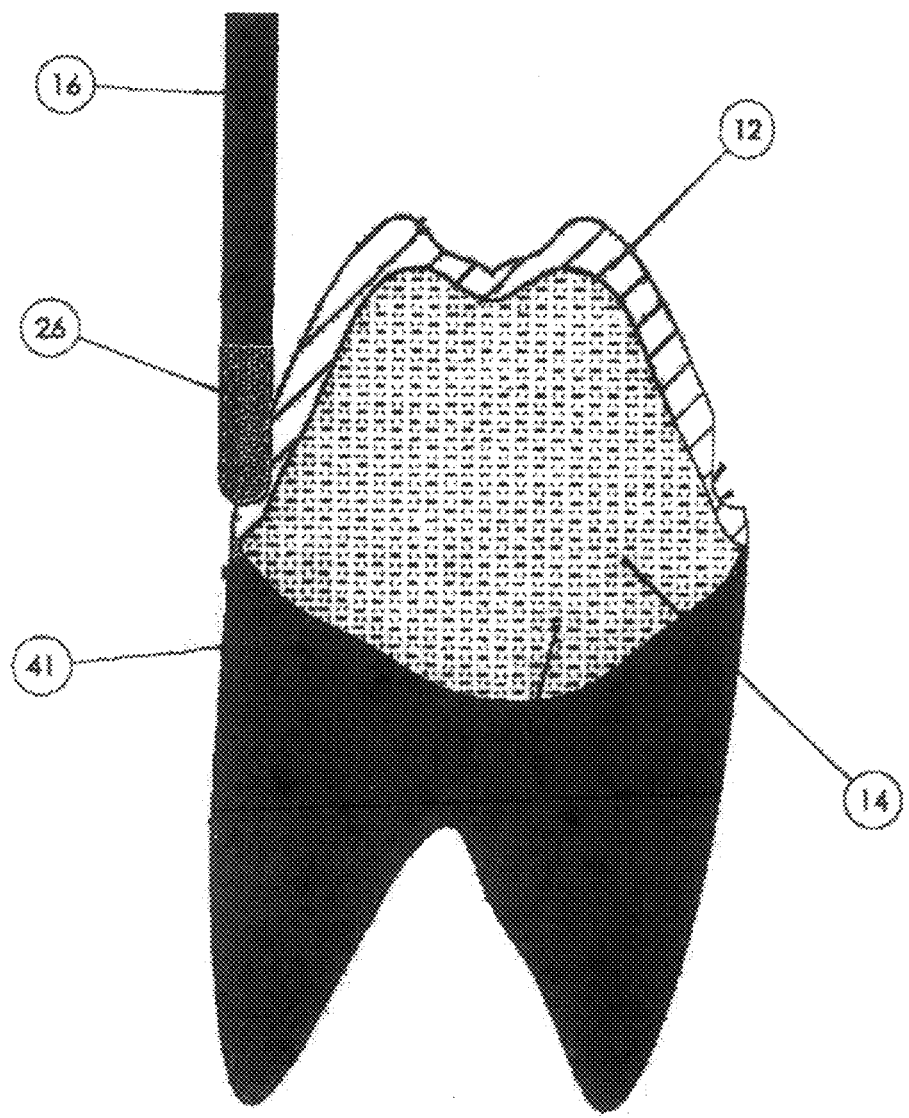
FIG. 2 shows a basic view of a tooth to be prepared.

The teaching of the invention for obtaining 3-D data of a prepared jaw area will be explained in principle using the figures. For reasons of simplicity a tooth 10 to be prepared is selected as jaw area. Such a tooth can be gathered from FIG. 2. In the case of tooth 10 its enamel 12 is to be ablated in the exemplary embodiment to such an extent that a stump remains on which, e.g., a cap for a denture such as a bridge is fastened. For the preparation of tooth 10 a rotating tool also to be designated as an abrasive pin—called drill 16 in the following for the sake of simplicity—is used that emanates from an instrument holder 18 and can be set in it in a replaceable manner and which is guided in a customary manner by a dentist performing the preparation.

The invention provides that simultaneously with the preparation of tooth 10 a final determination of contour takes place, that is, a determination of the course of the geometry of the surface of tooth stump 14. Consequently, a working and scanning is carried out simultaneously in order to have 3-D data of tooth stump 14 available after the end of the working, based on which data a denture can be produced. It is provided to this end that holder 18 has at least three optical markings 20, 22, 24 that can be, e.g., LEDs. They are detected by a stationarily arranged optical sensor 27 in order to determine in this manner the spatial position of the holder 18. The latter has an unambiguous position relative to drill 16, i.e. to its tip 26 that ablates tooth 10 and/or enamel 12, so that even the spatial position of drill tip 26 is determined from the spatial determination of position of holder 18. For this, it is necessary that a calibration of holder 18 designated in its entirety as dental instrument 28 is carried out with drill 16 beforehand. This takes place such a manner as is done with coordinate measuring devices operating in a tactile manner in which the sensor, that emanates from a holder, is calibrated on a normal such as a calibration sphere.

During the working of tooth 10 the spatial coordinates of holder 18 and therefore of drill tip 26 are determined via optical sensor 27 and supplied to a computer 30 in order to obtain data for a reconstruction with this data by means of a software such as CAD software with which reconstruction data a working machine 32 is controlled by, e.g., a CAM software, with which machine the denture such as a cap to be placed on prepared stump 14 is produced, e.g., by milling from a blank 34. Blank 34 can be produced from at least one mixed oxide powder from the group consisting of $Al_2O_3$, $TiO_2$, $MgO$, $Y_2O_3$ and zirconium oxide mixed crystal and can be a pre-sintered body.

During the preparation of tooth 10 the inner contour of the denture is determined by the spatial determination of holder 18 and therewith of drill tip 26. In a supplementary manner at least areas of the outer contour of the denture to be produced can be determined, especially in the area of the preparation boundary, therefore, in the direct vicinity of adjacent teeth when the drill is not actuated by guiding it on the jaw areas adjacent to tooth stump 14. Remaining data can be taken from a library.

Figure 3:
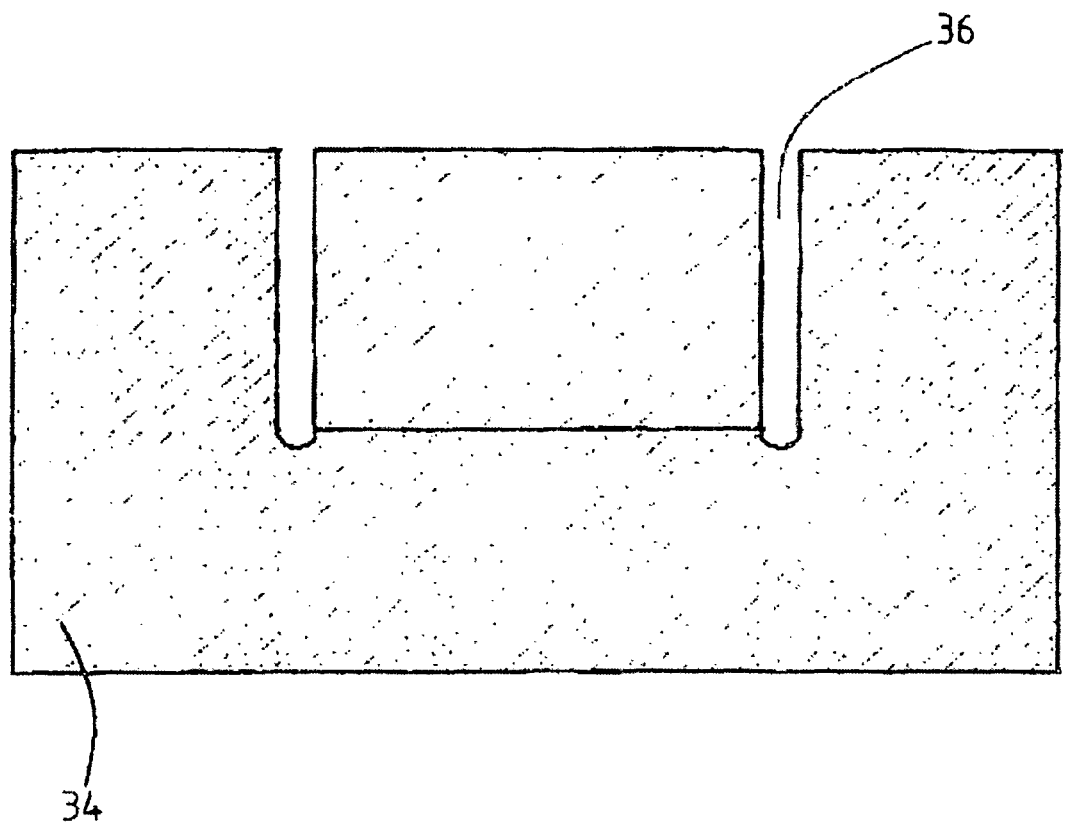
FIG. 3 shows a basic view of a fictitious blank at the beginning of the preparation of the tooth according to FIG. 2.
Figure 4:
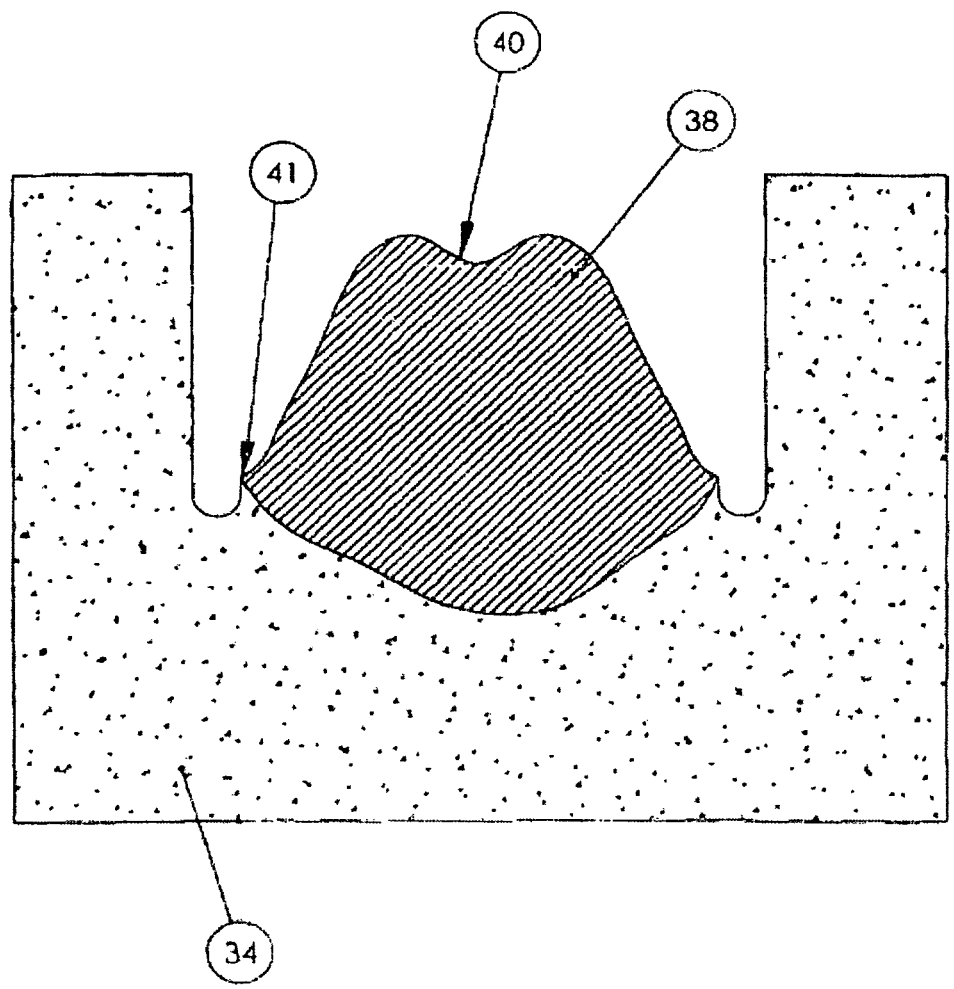
FIG. 4 shows the fictitious blank according to FIG. 3 after partial preparation of the tooth according to FIG. 2.

In order to determine the 3-D data from which the denture is produced, one can proceed according to the figures in accordance with FIGS. 3 and 4. Thus, FIG. 3 shows a spatial volume designated in the following as fictitious blank 34 inside which the data of the spatial coordinates of the denture to be produced are completely present, which consequently corresponds to a point cloud. As follows from FIG. 2, at first a moving of drill 16, i.e., of drill dip 26, along preparation boundary 41 of tooth 10 to be worked takes place in the exemplary embodiment so that a groove 36 is milled in fictitious blank 34 whose circumferential wall corresponds to that of stump 14. Accordingly, areas and coordinate values are removed from the spatial volume and therewith from the point cloud. Then the sides of tooth 10 are worked in order to obtain a contour 38 from blank 34 that corresponds to tooth stump 14. Finally, the occlusal area of tooth 10 is worked, i.e. the area 40 shown in FIG. 4. The envelope of fictitious blank 34 produced in this manner represents the 3-D data of prepared tooth stump 14, which data is processed by software in order to produce the inner contour of a denture to be placed on prepared tooth stump 14.

If a preparation starting from the preparation boundary takes place in accordance with the previously given explanations, this does not limit the invention. Also, the preparation can take place quasi from above downward. However, independently of the above, the preparation boundary 41 should be separately photographed, namely with a stationary, i.e., non-rotating tool after the preparation has taken place, that is, after its conclusion. For this, drill 16 can be turned off. A separate feeler can also be used in order to measure the preparation boundary in a tactile manner.

Separate feeler does not mean in this case that a special instrument must be used but rather the handle of the dental instrument can be used and provided with a special insert such as a feeler pin in order to explore the preparation boundary. However, there must be knowledge between the affected geometry of the feeler pin and the markings on the handle in order to make possible an unambiguous description of the preparation boundary.

Furthermore, the teaching of the invention can also be used if a standard abutment with a reference surface has already been inserted in the jaw area. In this case only a tactile scanning of the reference surface is required in order to produce a denture to be positioned in a positionally precise manner because in the case of a providing of an implant with a standard abutment (artificial tooth stump) the data of the artificial tooth stump (abutment) carrying the later crown is known.

In order to exclude measuring distortions that take place by a movement of the jaw of the patient in whose mouth a tooth is being prepared, it is further provided that a sensor or parts of a sensor is/are positioned stationarily to the jaw in order to offset the movement data against spatial coordinates of dental instrument 28. It can be provided that, e.g., an inertial platform 44 is arranged stationarily to the jaw, e.g., via a face clamp 42 or a bite block via which the movement of the jaw is imparted to sensor 27 and thus to drill 16 and its tip 26. However, there is also the possibility of positioning optical markings corresponding to markings 20, 22, 24 stationarily to the jaw which optical markings are then also detected by sensor 27. Care must of course be taken that the particular groups of markings emit optical radiation with differentiating wavelengths.

Instead of sensor 27 detecting the movement of dental instrument 28, another optical sensor calibrated to the position of sensor 27 can also be used to take account of the jaw movement.

The preparation edge is scanned after completion of the preparation.

The invention claimed is:

1. A process for producing a denture, comprising the steps of:
    ablating a tooth or tooth stump in a jaw area to a desired contour using a rotating dental instrument,
    measuring positions of the rotating dental instrument during the ablating step using an optical device;
    obtaining digital 3-D data of said tooth or tooth stump having said desired contour based on the measured positions of the rotating dental instrument after the ablating step;
    processing the digital 3-D data using CAD software;
    producing the denture based on the processed 3-D data;
    wherein an inner contour of said denture is determined and calculated from said processed 3-D data, and an outer contour of said denture is determined and calculated from data taken from a library or from scanning said jaw area.

2. The process according to claim 1, wherein the rotating dental instrument is provided with optically effective markings that are detected by a stationarily arranged optical sensor for spatial determination of the positions of the rotating dental instrument.

3. The process according to claim 1, wherein the rotating dental instrument comprises a tool for preparing the jaw area.

4. The process according to claim 1, wherein, prior to the ablating step, the rotating dental instrument is calibrated by scanning a normal.

5. The process according to claim 1, wherein the rotating dental instrument comprises a tool holder with a replaceable tool.

6. The process according to claim 1, the positions of the rotating dental instrument are determined by taking into consideration a movement of the jaw area relative to the rotating dental instrument.

7. The process according to claim 1, wherein a position sensor is provided and arranged stationarily relative to the jaw area.

8. The process according to claim 7, wherein an inertial platform is said position sensor.

9. The process according to claim 1, wherein optical markings are assigned to the jaw area and are stationary to the jaw area, said optical markings are detected by an optical sensor.

10. The process according to claim 9, wherein light source or reflector are used as said optical markings.

11. The process according to claim 1, wherein the denture is produced by a working machine from a pre-sintered blank or by a building-up process.

12. The process according to claim 1, wherein said rotation dental instrument has a rotating function, wherein a boundary of the jaw area is determined with the rotating dental instrument while not actuating its rotating function by guiding said rotating dental instrument on said jaw area.

13. The process according to claim 12, wherein the boundary of the jaw area is determined after the ablating.

14. The process according to claim 1, wherein a boundary of the jaw area is determined with a separate feeler or with a feeler pin.

15. The process according to claim 1, wherein a power change that occurs when the rotating dental instrument comes in contact with the jaw area is used to start the measuring.

16. The process according to claim 3, wherein the tool is a drill.

17. The process according to claim 4, wherein the normal is a sphere.

18. The process according to claim 10, wherein the light source is an LED.

\* \* \* \* \*